United States Patent [19]

Neoh

[11] Patent Number: 5,470,604
[45] Date of Patent: Nov. 28, 1995

[54] APPARATUS AND METHOD FOR SPREADING RESIST ON A WAFER AND DETECTING BUBBLES IN THE RESIST

[75] Inventor: Soon E. Neoh, Singapore, Singapore

[73] Assignee: Chartered Semiconductor Manufacturing Pte LTD, Singapore, Singapore

[21] Appl. No.: 267,757

[22] Filed: Jul. 5, 1994

Related U.S. Application Data

[63] Continuation of Ser. No. 44,164, Apr. 8, 1993, abandoned.

[51] Int. Cl.⁶ .............................. B05D 1/00; B05C 11/00; G01N 7/00
[52] U.S. Cl. .............................. 427/8; 118/688; 118/712; 73/19.1
[58] Field of Search ........................ 118/688, 712, 118/320; 73/19.01, 19.1; 324/663; 222/154; 427/445, 421, 457, 561, 8

[56] References Cited

U.S. PATENT DOCUMENTS

| | | | |
|---|---|---|---|
| 3,915,155 | 10/1975 | Jacobson et al. | |
| 3,921,622 | 11/1975 | Cole . | |
| 3,974,681 | 8/1976 | Namery | 73/19 |
| 4,014,206 | 3/1977 | Taylor | 73/19 |
| 4,068,521 | 1/1978 | Cosentino et al. | 73/19 |
| 4,236,880 | 12/1980 | Archibald . | |
| 4,418,565 | 12/1983 | St. John | 73/19 |
| 4,599,888 | 7/1986 | Hufton et al. | 73/19.11 |
| 4,607,520 | 8/1986 | Dam | 73/19 |
| 4,651,555 | 3/1987 | Dam | 73/19 |
| 4,899,686 | 2/1990 | Toshina | 118/50 |
| 5,134,962 | 8/1992 | Amada et al. | 118/688 |
| 5,191,795 | 3/1993 | Fellingham et al. | 73/599 |
| 5,211,626 | 5/1993 | Frank et al. . | |
| 5,313,818 | 5/1994 | Sayka et al. | 73/19.1 |
| 5,394,732 | 3/1995 | Johnson et al. | 73/19.1 |

*Primary Examiner*—David L. Lacey
*Assistant Examiner*—Steven P. Griffin
*Attorney, Agent, or Firm*—George O. Saile; William S. Robertson

[57] ABSTRACT

A station for coating a semiconductor wafer with a photoresist is provided with a detector for bubbles that may occur in the resist that is supplied to the wafer. The resist is carried to the coating apparatus by a plastic tube. A commercially available capacitance detector is positioned to detect the dielectric constant of the combination of the tube, the resist, and any bubbles in the resist. The dielectric constant of the bubbles is lower than the dielectric constant of the resist, but the difference is not sufficient for detecting the bubbles with the capacitance detector alone. A metal backing plate is located on the side of the tube opposite the detector and enhances the operation of the detector sufficiently to detect bubbles of various sizes.

6 Claims, 1 Drawing Sheet

APPARATUS AND METHOD FOR SPREADING RESIST ON A WAFER AND DETECTING BUBBLES IN THE RESIST

RELATED APPLICATION

This application is a continuation of application of Ser. No. 08/044,164 filed Apr. 8, 1993, now abandoned.

FIELD OF THE INVENTION

This invention relates to apparatus for the manufacture of semiconductor devices, and more specifically to apparatus for detecting bubbles in a photoresist that is supplied to a wafer coating station.

INTRODUCTION

The apparatus and related process for coating a semiconductor wafer are well known, but it will be helpful to review the features and terminology that particularly apply to this invention. The resist station has a chuck for holding the wafer and a nozzle for applying a measured amount of resist to the exposed surface of the wafer. While the resist is being applied, the chuck is spun and the resist is spread over the wafer surface by centrifugal force.

The resist is held in any suitable container and it is carried to the resist spreader nozzle by any suitable means, commonly by a plastic tube. From a more general standpoint, the tube is a dielectric.

THE BUBBLE PROBLEM

Air bubbles can appear in the resist, and these bubbles can damage the resist coating. The common practice is to stop the process when the effects of bubbles are noticed, to clear the system of bubbles, and to restart or continue the process.

Therefore it would be advantageous to detect the bubbles as close to the bubble source as possible.

THE PRIOR ART

U.S. Pat. No. 4,899,686 discusses the bubble problem.

SUMMARY OF THE INVENTION

The dielectric constants of the resist and the tube are sufficiently different from the dielectric constant of air bubbles that it would seem to be possible to detect the bubbles with a commercially available capacitance sensor. However, these detectors have been found to be unable to detect bubbles sufficiently well for use in a semiconductor manufacturing line.

According to this invention, a conductive backing plate is located close to the supply tube on the opposite side of the tube from the capacitive sensor. The plate enhances the operation of the capacitive tester, probably by its effect on the electrostatic field of the capacitive sensor, as will be discussed later.

Other objects and features of the invention will be apparent from the description of the preferred embodiment of this bubble detector.

THE PREFERRED EMBODIMENT

The Conventional Resist Supply System

Figure 1:
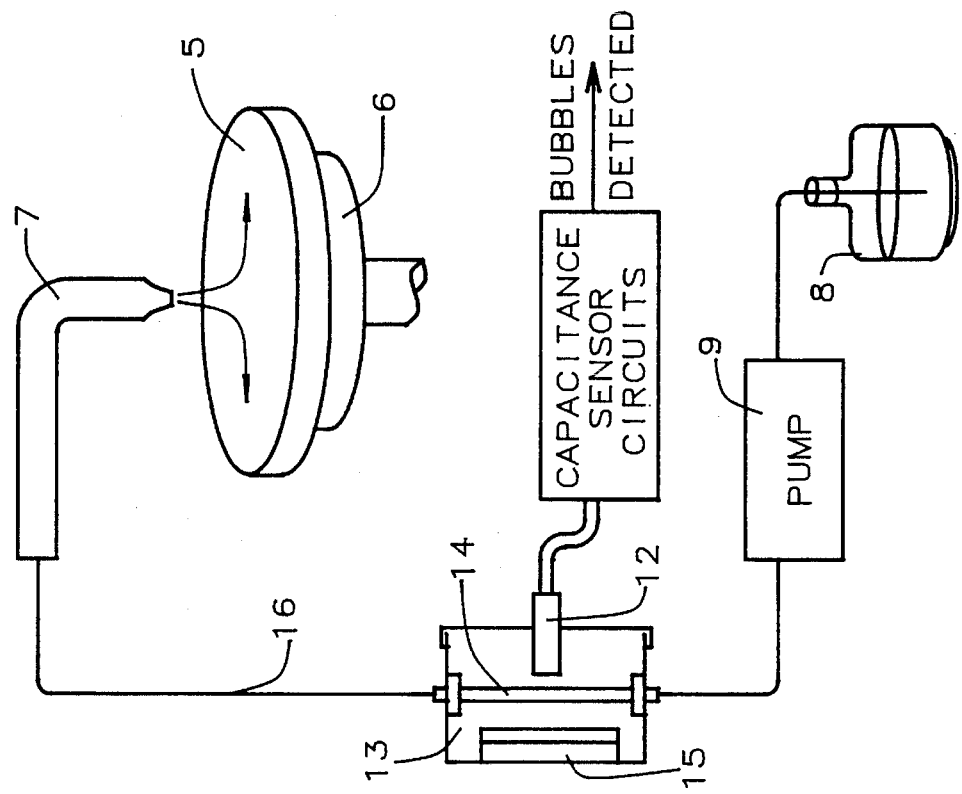
FIG. 1 is a schematic of a resist coating station with the bubble detector of this invention.

FIG. 1 shows a conventional wafer coating station with a wafer 5, apparatus 6 for holding and spinning the wafer, a nozzle 7 for applying a photoresist to the wafer surface, a container 8 for the resist, a resist pump 9 and a plastic tube 16 that carries the resist to the nozzle.

The tube 16 is conventionally made of PTFE ("TEFLON"). The tube commonly has an outside diameter of about ¼, and this tubing size is preferred in the method and apparatus of this invention.

The Bubble Problem

A single bubble might be 5–6 mm in diameter and will almost fill the tube. Alternatively, the resist may have a mass of small bubbles that almost fill the tube or only a single small bubble. Thus the bubbles present a difficult problem for a capacitance sensor, and a capacitance sensor alone has been unable to detect bubbles satisfactorily The conventional capacitive sensor Capacitance sensors are commercially available and many of these sensors will operate satisfactorily in the detector of this invention. These bubble detectors operate by producing an electrostatic field in the region that is to be tested. The results of the test can be interpreted for example as the dielectric constant of the material in which the field is established.

The operation of the apparatus of this invention can be understood by considering a simplified description of the conventional capacitance sensor. The sensor has an electrode located in its tip. The electrode is connected to a circuit that supplies an oscillatory voltage and senses the oscillatory current in the electrode circuit.

The effect of the dielectric constant

The bubble detector responds to the difference in dielectric constant between the bubbles and the resist. The resist bubbles are air, which has a dielectric constant of 1, which is low in relation to the other materials that are relevant to this explanation. The dielectric constant of the PTFE tube is about 2, and the dielectric constant of the resist is about 3.5 to 5.

To simplify the explanation, the tube and the resist (without any bubbles) can be thought of as a series of dielectrics with these values. Similarly, the simple case in which a bubble fills the tube can be thought of as the series of dielectrics that have dielectric constants of about 2 for the tube and 1 for the bubble.

In a hypothetical situation that does not correspond to the wafer coating situation, the commercial capacitance sensor would produce one signal for the tube and resist without the bubbles and it would produce a distinguishable signal for the tube and the bubble.

The backing plate

The combination of the backing plate and the commercial capacitance sensor does produce this distinguishable signal for bubbles in the delivery line 16.

FIG. 1 shows a section of tubing 14, the capacitance sensor 12, and a housing 13 that supports the sensor and the tube section 14 for the detector to sense the dielectric constant of the tube and its contents. A backing plate 15 is mounted in the housing on the side of the tube opposite the detector and close to the tube section 14.

Figure 2:
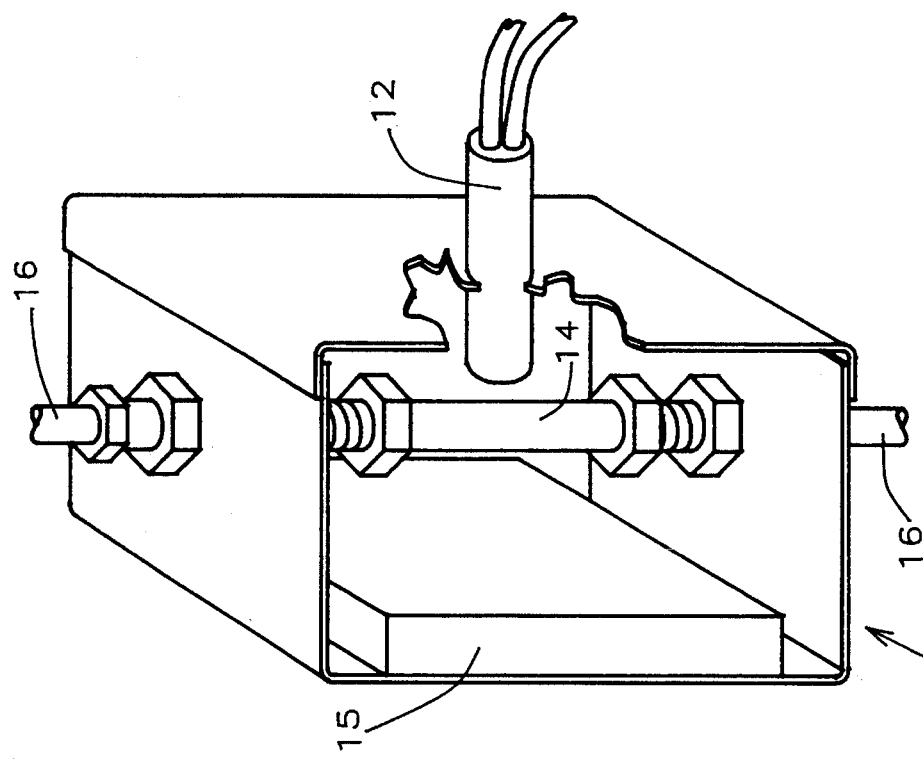
FIG. 2 is an isometric drawing of the sensor capacitance, the backing plate, and a supporting structure.

FIG. 2 shows the preferred housing structure. The housing 13 preferably is made with rectangular sides. A section 14 of tubing in the housing is preferably connected to the rest of the delivery line 16 by removable fittings so the sensor 12, its housing 13, and the associated section 14 of line 16 can be removed from the coating station. The capacitance sensor 12 is held in place by suitable means such as the surrounding wall of the corresponding side of the housing.

The backing plate is a metal plate that is mounted on the back wall of the housing to be close to the tube. The backing plate has a suitable thickness to enhance the operation of the capacitance sensor sufficiently to detect bubbles in the resist. The tube is sufficiently thick to provide the conductance to serve as an electrode in the detector system, but a size that is suitable for construction purposes will ordinarily be sufficient for electrical purposes. As FIG. 1 shows, the metal backing plate is flat and is located parallel to the tubing where bubbles are to be detected. From an electrical standpoint, the backing plate is thick enough to form a ground for the capacitance detector. Some bubbles that cannot be distinguished from resist without the backing plate can be detected with the detector using the backing plate.

Other Embodiments

The detector with the backing plate should operate satisfactorily with tubing of a different size, for example with ½ tubing and a larger capacitive sensor. Those skilled in the art will recognize other modifications of the preferred embodiment within the spirit of the invention and the intended scope of the claims.

I claim:

1. In an apparatus for spreading a resist on a semiconductor wafer including a supply of a resist having a predetermined dielectric constant, a nozzle for applying the resist to the wafer, and a tube made of dielectric material carrying the resist from the supply to the nozzle, and a bubble detector for bubbles in the resist flowing in the tube, wherein the improvement comprises said bubble detector comprising, a capacitance sensor having electrode means for establishing an electric field in a subject to be tested and having a circuit for signaling the dielectric constant of the subject, and means mounting the capacitance sensor on one side of the tube and near the tube to sense the dielectric constant of the combination of the tube, the resist in the tube, and any bubbles in the resist, and a metal backing plate located near the tube on the side of the tube opposite the capacitance sensor, the backing plate of a thickness to form an electrical ground for the capacitance sensor.

2. The apparatus of claim 1 wherein the metal backing plate is flat and is located parallel to the tubing where bubbles are to be detected.

3. The apparatus of claim 2 wherein the detector includes housing for holding the capacitance sensor, the backing plate, and the tube in predetermined relative positions.

4. The apparatus of claim 3 wherein the capacitance sensor is connected to and supported by a side wall of the housing (13) and the tube (16) includes a section (14) located in the housing and wherein said section is separable from the rest of the tube for removing the housing, the section, and the bubble detector from the rest of the tube and the apparatus for spreading resist.

5. A method for spreading a resist coating evenly on a wafer, wherein the resist coating is adversely affected by bubbles in the resist, the method comprising the following steps, providing a resist station including a resist nozzle and a means for holding the wafer to receive resist from the nozzle, providing a resist supply and creating a flow of the resist from the resist supply through a resist delivery line to the nozzle, the resist being subject to bubble formation that may interfere with the resist coating, monitoring the flow of the resist through the delivery line with a capacitance sensor located on one side of the delivery line and a conductive plate of a thickness to form an electrical ground for the capacitance sensor located near the capacitance sensor and on the side of the delivery line opposite the sensor, and stopping the spreading of the resist on the wafer if bubbles in the delivery line are detected during said monitoring step.

6. The method of claim 5 wherein the step of monitoring the flow of the resist with a capacitance sensor and a conductive plate includes the step of establishing an electrical ground for the capacitance sensor with the conductive plate.

* * * * *